(12) United States Patent
Wang et al.

(10) Patent No.: US 9,260,743 B2
(45) Date of Patent: Feb. 16, 2016

(54) RAPID AND ACCURATE ANALYSIS OF PROTEIN SIALYLATION

(75) Inventors: Zihao Wang, Cary, NC (US); Jessica Sloan, Garner, NC (US); Kevin Wee, Wake Forest, NC (US)

(73) Assignee: GRIFOLS. S.A., Barcelona (ES)

( * ) Notice: Subject to any disclaimer, the term of this patent is extended or adjusted under 35 U.S.C. 154(b) by 0 days.

(21) Appl. No.: 14/232,783

(22) PCT Filed: Jul. 5, 2012

(86) PCT No.: PCT/ES2012/070501
§ 371 (c)(1),
(2), (4) Date: Jan. 14, 2014

(87) PCT Pub. No.: WO2013/011178
PCT Pub. Date: Jan. 24, 2013

(65) Prior Publication Data
US 2014/0162299 A1     Jun. 12, 2014

Related U.S. Application Data

(60) Provisional application No. 61/507,643, filed on Jul. 14, 2011.

(51) Int. Cl.
*C12Q 1/34* (2006.01)
*C12Q 1/54* (2006.01)
*B01D 15/36* (2006.01)
*G01N 30/88* (2006.01)

(52) U.S. Cl.
CPC ............... *C12Q 1/54* (2013.01); *B01D 15/363* (2013.01); *C12Q 1/34* (2013.01); *G01N 2030/8831* (2013.01); *G01N 2333/924* (2013.01); *G01N 2333/938* (2013.01)

(58) Field of Classification Search
None
See application file for complete search history.

(56) References Cited

U.S. PATENT DOCUMENTS
2011/0086362 A1     4/2011  Wang et al.

FOREIGN PATENT DOCUMENTS
WO      WO 03090695 A2     11/2003

OTHER PUBLICATIONS

Yamamoto ("Copurification and separation of beta-galactosidase and sialidase from porcine testis" The International Journal of Biochemistry (1987), 19(5) 435-442, Abstract provided).*
Hounsell, Glycoanalysis Protocols Methods in Molecular Biology, vol. 76, Second Edition, 1998, Humana Press, Totowa New Jersey, Chapters 4-6, pp. 53-107.*

(Continued)

*Primary Examiner* — Kade Ariani
*Assistant Examiner* — Charles Zoltan Constantine
(74) *Attorney, Agent, or Firm* — RatnerPrestia

(57) ABSTRACT

The invention relates to methods and kits for the analysis of the sialylation of gluco-proteins. The samples of gluco-protein are incubated separately under three conditions: with beta-galactosidase, with beta-galactosidase+alpha-sialidase, and without an enzyme. After the enzyme treatment, high performance anion exchange chromatography with pulsed amperometric detection (HPAEC PAD) is used to make a quantitative determination of the total galactose in the sample, the non sialylated galactose and the exogenous galactose in the medium. The determination of said values makes it possible to deduce the percentage of sialylation of the gluco-protein.

7 Claims, 6 Drawing Sheets

(56) References Cited

OTHER PUBLICATIONS

Mechref "Mass Spectrometric Mapping and Sequencing of N-Linked Oligosaccharides derived from Submicrogram Amounts of Glycoprotein", Analytical Chemistry, vol. 70, 1998, 455-463.*

Hemmerich et al., Structure of the O-glycans in GlyCAM-1, an endothelial-derived ligand for L-selectin. The Journal of Biological Chemistry, 1995, vol. 270 (20), pp. 12035-12047, especially pp. 12036-12038; figures 1-2.

Bhavanandan et al., Identification of the glycosidically bound sialic acid in mucin glycoproteins that reacts as "free sialic acid" in the Warren assay. Glycobiology, 1998 vol. 8(11), pp. 1077-1086, especially pp. 1081, 1085.

Rohrer et al., Analysis of the N-acetylneuraminic acid and N-glycolylneuraminic acid contents of glycoproteins by high-pH anion-exchange chromatography with pulsed amperometric detection (HPAEC/PAD). Glycobiology, 1998 vol. 8(1), pp. 35-43, the whole document.

International search report dated Sep. 24, 2012 in corresponding PCT Application No. PCT/ES2012/070501 filed Jul. 5, 2012.

* cited by examiner

RAPID AND ACCURATE ANALYSIS OF PROTEIN SIALYLATION

CROSS REFERENCE TO RELATED APPLICATIONS

This application is a 371 application of International Application No. PCT/ES2012/070501, filed Jul. 5, 2012, which claims priority to U.S. Provisional Patent Application No. 61/507,643, filed Jul. 14, 2011, each of which is incorporated by reference in its entirety herein.

TECHNICAL FIELD

Described herein are analytical methods for analyzing protein sialylation.

BACKGROUND

Many proteins require glycosylation for their biological function. Often, the terminal, "capping," carbohydrates of glycosylic chains are sialic acid residues. Sialic acids comprise a family of N- and O-linked neuraminic acids. N-linked sialic acids are formed by linking acetyl or glycolyl moieties to the amino residue of neuraminic acid, forming N-acetyl-neuraminic acid (Neu5Ac) and N-glycolylneuraminic acid (Neu5Gc), respectively. If the amino group of neuraminic is substituted with a hydroxyl moiety, this yields 3-deoxy-D-glycero-D-galacto-2-nonulosonic acid (KDN). O-linked sialic acids are formed by the substitutions of one or more of the hydroxyl groups of Neu5Ac, Neu5Gc, or KDN with methyl, acetyl, lactoyl, sulfate, or phosphate groups. Accordingly, a large and diverse population of sialic acids exists.

Further, there is considerable interest in analyzing protein sialylation, in general, because of the numerous biological functions attributed to these modifications. Sialylation can be important for the pharmacokinetics and efficacy of protein biotherapeutics. Consequently, several analytical methods have been developed to evaluate the sialic acid content of glycoproteins. For example, antibody-based assays can be used to identify particular carbohydrate moieties.

Terminal sialic acid resides can be enzymatically detached from the glycoprotein of interest and analyzed by HPLC. However, each of these methods has shortcomings and typically requires pure samples or high concentrations. Conventional methods used by the biopharmaceutical industry suffer from poor accuracy, high data variability, and they cannot be used with complex culture media due to matrix interference. The method described herein overcomes such shortcomings and provides accurate and reproducible quantitation of protein sialylation.

Collectively, the method described herein comprises two steps: (1) an enzymatic reaction is used to hydrolyze the galactose and sialic acid residues from the glycoproteins; and (2) an ion-exchange chromatography method is used to separate and quantify the galactose residues. The enzymatic portion of the method involves the release of exposed (uncapped) terminal galactose residues by the specific exo-glycosidase, β-(1-4)-galactosidase (β-galactosidase), while the terminal sialic acid residues are released by α-(2-3,6,8,9)-sialidase (α-sialidase). Prior to digestion, a sample is divided among at least three tubes. The first tube, Reaction A, is a background sample, and comprises the enzyme reaction buffers only. The second tube, Reaction B, is reacted with β-galactosidase that cleaves all galactose residues that are not capped by sialic acids. The third tube, Reaction C, is co-digested with both neuraminidase and β-galactosidase. The neuraminidase enzyme removes the capping sialic acids and permits β-galactosidase to cleave all of the exposed galactose residues. High Performance Anion-exchange chromatography with Pulsed Amperometric Detection (HPAEC PAD) is then used to determine the amount of galactose present in the three samples. The ratio of uncapped galactose (i.e., Reaction B) to total galactose (i.e., Reaction C) is used to calculate percent capping of galactose residues, while also accounting for any free galactose present in the media (Reaction A).

SUMMARY

Described herein are methods for analyzing the sialylation of a protein.

Also described is a method for determining the sialylation content of a protein comprising: (a) preparing a protein for analysis; (b) enzymatically treating the prepared protein comprising: dividing the prepared protein into a plurality of protein samples comprising (i) at least one protein sample as a media sample (Reaction A); (ii) adding at least β-galactosidase to at least one protein sample (Reaction B); (iii) adding at least β-galactosidase, and α-sialidase to at least one other protein sample (Reaction C); and incubating the plurality of protein samples; and (c) analyzing the plurality of protein samples using HPAEC-PAD chromatography; (d) determining a carbohydrate content for the plurality of protein samples; and (e) calculating a percent sialylation for the protein.

Also described is a method further comprising (f) analyzing a plurality of positive and negative controls using HPAEC-PAD chromatography; (g) analyzing a plurality of standards using HPAEC-PAD chromatography; and (h) comparing the plurality of protein samples to the plurality of standards and controls.

Also described is the use of HPAEC-PAD chromatography for determining the sialylation content of a protein comprising: (a) preparing a protein for analysis; (b) enzymatically treating the prepared protein comprising: dividing the prepared protein into a plurality of protein samples comprising (i) at least one protein sample as a media sample (Reaction A); (ii) adding at least β-galactosidase to at least one protein sample (Reaction B); (iii) adding at least β-galactosidase, and α-sialidase to at least one other protein sample (Reaction C); and incubating the plurality of protein samples; and (c) analyzing the plurality of protein samples using HPAEC-PAD chromatography; (d) determining a carbohydrate content for the plurality of protein samples; and (e) calculating a percent sialylation for the protein.

Also described is the use further comprising: (f) analyzing a plurality of positive and negative controls using HPAEC-PAD chromatography; (g) analyzing a plurality of standards using HPAEC-PAD chromatography; and (h) comparing the plurality of protein samples to the plurality of standards and controls.

Also described is a kit for determining the sialylation content of any protein comprising: at least one container comprising a plurality of containers comprising premeasured quantities of a galactosidase and a sialidase; optionally, containers containing at least one buffer composition, a positive control sample, a negative control sample, and carbohydrate standards, and instructions describing a method for determining the sialylation content of a protein, comprising descriptions of: (a) preparing a protein for analysis; (b) enzymatically treating the prepared protein comprising: dividing the prepared protein into a plurality of protein samples comprising (i) at least one protein sample as a media sample (Reaction A); (ii) adding at least β-galactosidase to at least one protein sample (Reaction B); (iii) adding at least β-galactosidase, and α-sialidase to at least one other protein sample (Reaction C); and incubating the plurality of protein samples; and (c) analyzing the plurality of protein samples using HPAEC-PAD chromatography; (d) determining a carbohydrate content for the plurality of protein samples; and (e) calculating a percent sialylation for the protein.

Also described is a kit further comprising: (f) analyzing a positive and negative control using HPAEC-PAD chromatography; (g) analyzing a plurality of standards using HPAEC-PAD chromatography; and (h) comparing the plurality of protein sample results to the results of the plurality of standards.

DETAILED DESCRIPTION

Figure 1:
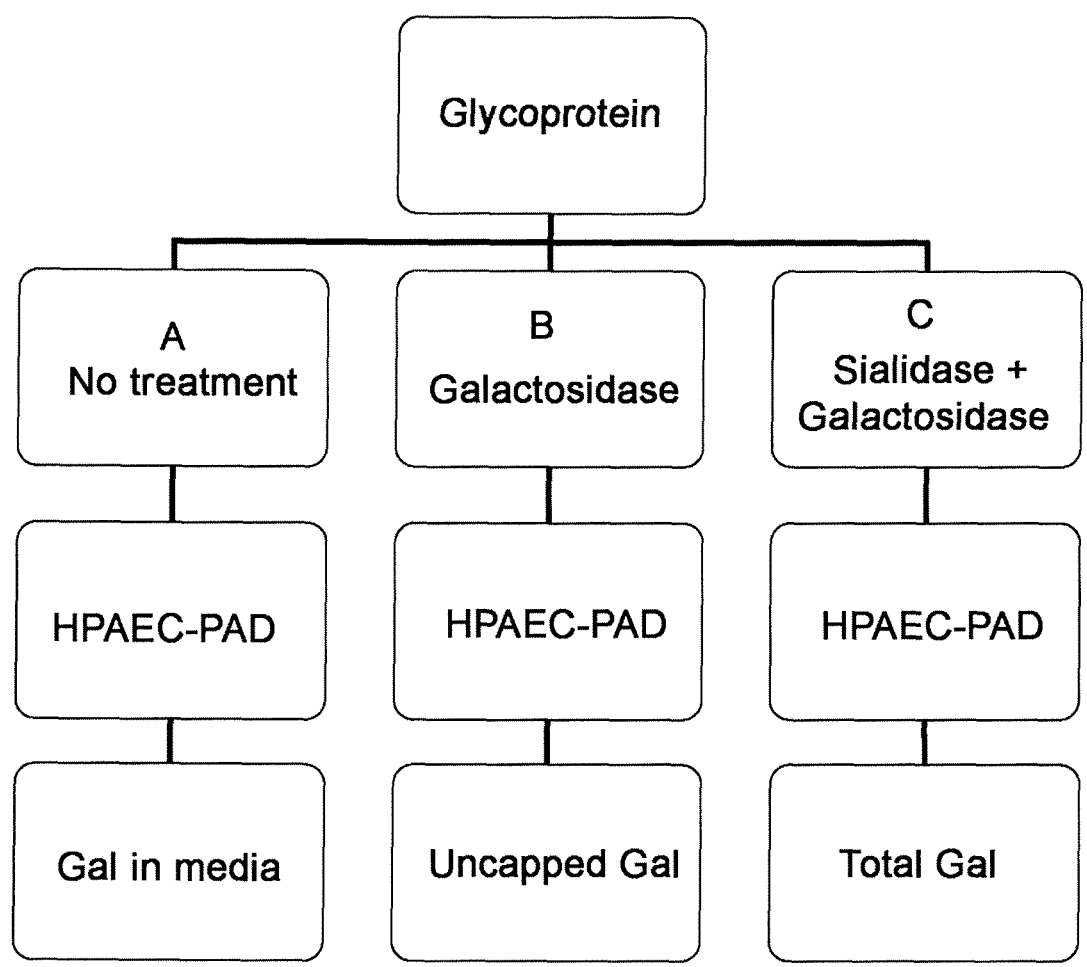
FIG. 1 shows a schematic of Reactions A, B, and C, and the data that is obtained from each respective reaction. The percent sialylation capping can be determined from the quotient of the differences in Reactions C and B and Reactions C and A, respectively. See Equation 1.

An example of a protein that can be analyzed using the method described here in is alpha 1-proteinase inhibitor (also known as alpha 1-antitrypsin). Alpha 1-proteinase inhibitor is a naturally occurring serpin glycoprotein that is involved in protecting cells from protease enzymes involved in clotting and inflammation. The absence of alpha-1 protease inhibitor, alpha 1-antitrypsin deficiency, leads to respiratory disorders such as emphysema and chronic obstructive pulmonary disease (COPD). Accordingly, there is interest in using alpha-1 protease inhibitor as a biotherapeutic to treat alpha-1 protease inhibitor deficiency related illnesses. Recombinant alpha-1 proteinase inhibitor (recAlpha-1) was engineered for secretion by the PerC6 cell line with N-linked glycan carbohydrate structures that are partially or fully capped by terminal sialic acids (N-acetylneuraminic acids). A decrease in the quantity of terminal sialic acids has been shown to reduce recAlpha-1's serum half-life. Therefore, it is important to know the percent of galactose residues capped by salic acids in recAlpha-1 when investigating its function or efficacy as a therapeutic drug.

EXAMPLES

Example 1

Sample Preparation for Analysis and Enzymatic Digestion

A method for the determination of the sialylation content of a glycoprotein is described herein. The method begins with the preparation of a protein sample for enzymatic hydrolysis of the carbohydrate moieties. Accordingly, the protein must be brought into conditions compatible with the enzymatic reactions, including adjusting the protein concentration, removing solution components such as dissolved salts, buffers, other proteins, carbohydrates, excipients, etc., which might interfere with the enzyme(s). As used herein, the term "prepared" or the phrase "preparing a protein for analysis" describes the process of removing solution components that might interfere with the enzymatic hydrolysis and diluting the protein solution to an optimal concentration for the assay with deionized water.

At least two non-limiting exemplary methods can be used to prepare protein solution components from proteins for analysis: (1) dialysis against deionized water or (2) centrifugal filtration (also called spin filtration). In both cases, a semi-permeable membrane with a specified molecular weight cut-off (MWCO) was used to remove lower-molecular weight species while retaining the analyte protein of interest. Useful MWCO ranges include 1 kDa, 2.5 kDa, 5 kDa, 10 kDa, 20 kDa, 50 kDa, 100 kDa, 250 kDa, and 500 kDa. In the dialysis procedure, the protein was inserted into a dialysis membrane and dialysed against an excess of deionized water or suitable buffer and/or salt solution for at least 4 hours at 4° C.

Alternatively, instead of being dialyzed, a protein sample can be prepared for the enzymatic digestion by centrifugal filtration. During centrifugal filtration, the protein solution was centrifuged against a semi-permeable membrane with a specified MWCO. Solution components with molecular weights below the MWCO pass through the filter during centrifugation, whereas the protein and higher molecular weight species are retained. Typically, the protein solution was concentrated during spin filtration, owing to water passing through the semi permeable membrane. Generally, as a non-limiting example, a 10 kDa spin filter was used according to the manufacturer's instructions for preparing the protein sample.

Prior to enzymatic digestion, protein samples were also diluted to a concentration of 1.0 to 1.5 mg/mL with deionized water so that they would be within the linear range of the assay. Once samples were diluted, at least one reaction for each condition (i.e., A, B, and C) was assembled. The prepared protein solution was divided into at least three samples for enzymatic de-glycosylation. See FIG. 1. Reaction A was the background control (to control for exogenous galactose). This reaction consists of only the buffers for the enzymatic reactions and serves as a control for carbohydrates that may exist in the medium comprising the protein analyte. Reaction B contained β-galactosidase, which hydrolyzed un-sialylated carbohydrate groups, but not those that were "capped" with sialyl groups. Reaction C contained both α-sialidase and β-galactosidase. In this reaction, α-sialidase hydrolyzed the capping sialyl moieties, which then permitted β-galactosidase to hydrolyze all of the carbohydrate groups. In this combined α-sialidase and β-galactosidase reaction, all glycosylation (i.e., sialylated and unsialylated) was removed from the protein, whereas in the β-galactosidase reaction, only the un-capped (unsialylated) carbohydrate groups were removed. The components for the three reaction conditions are shown in Table 1.

TABLE 1

Glycosylase Reaction Conditions

| Reaction | Deionized Water (μL) | Galactosidase Reaction Buffer (μL) | Sialidase Reaction Buffer (μL) | β-(1-4)-Galactosidase (μL) | α-(2-3,6,8,9)-sialidase (μL) |
|---|---|---|---|---|---|
| A—Background | 12 | 4 | 4 | 0 | 0 |
| B—β-galactosidase | 10 | 4 | 4 | 2 | 0 |
| C—β-galactosidase + α-sialidase | 8 | 4 | 4 | 2 | 2 |

The separate reactions were prepared in multiples based on number of samples to be digested. For each digest, 45 μL of sample was added to three separate tubes. Subsequently, 20 μL of the appropriate enzyme reaction A, B, or C was added to the tube indicated for that reaction type and heated on a thermo-mixer at 37° C., shaking moderately, for between 2.5 hours to 4 hours. The reaction was quenched by incubation at 90° C. for 5 minutes.

Once the digests were completed, the samples were prepared for chromatographic analyses by combining 30 μL of sample and 20 μL of 0.02 mg/mL deoxyribose standard in a vial and mixing thoroughly. The samples were then placed on a HPLC autosampler at 10° C. and run using the chromatographic method described in Example 2

Example 2

Chromatographic Methodology

High Performance Anion Exchange Chromatography with Pulsed Amperometric Detection (HPAE-PAD) analysis was performed on Dionex ICS-3000 ion chromatography systems with single pumps, thermostatted autosamplers set to 10° C., and electrochemical detection units (Dionex, Sunnyvale, Calif.). Disposable gold (Au) electrodes were used for pulsed amperometric detection (PAD) (Dionex Prod. No. 060139). The waveform used for sample analysis was based on Dionex Technical Note 21, which describes optimal settings for PAD of carbohydrates as shown in Table 2. See Dionex Technical Note 21, Optimal Settings for Pulsed Amperometric Detection of Carbohydrates Using the Dionex ED40 Electrochemical Detector, Dionex (1998).

TABLE 2

Dionex Recommended Optimal Waveform Settings for PAD of Carbohydrate Samples

| Time | Potential (V) | Integration |
|---|---|---|
| 0.00 | +0.1 | |
| 0.20 | +0.1 | Begin |
| 0.40 | +0.1 | End |
| 0.41 | −0.2 | |
| 0.42 | −0.2 | |
| 0.43 | +0.6 | |
| 0.44 | −0.1 | |
| 0.50 | −0.1 | |

Chromotography was performed using a Dionex CarboPac PA10 4×250 mm anion exchange column (Dionex Prod. No. 046110) with an in-line CarboPac PA10 4×50 mm guard column (Dionex Prod. No. 046115), and a 4×50 mm Amino Trap column (Dionex Prod. No. 046112) to bind desialylated protein and prevent its adsorption to the column.

The first mobile phase (A) contained 20 mM NaOH and was used for isocratic separation at a 1 mL/min flow rate for 30 minutes (the initial run time was 28 minutes but was extended to 30 minutes during development to allow more time for re-equilibration at 100% mobile phase A). The second mobile phase (B) contained 500 mM NaOH and was used for column elution, column cleaning, and electrode cleaning. The chromatographic elution method, including the ramp wash using the A and B mobile phases is shown in Table 3. The sample injection volume was 20 μL. Data analyses were performed using Chromeleon® 6.8 Chromatography Data Analysis System software (Dionex).

TABLE 3

HPAE-PAD Chromatography Elution Method

| Time (min) | % A (20 mM NaOH) | % B (500 mM NaOH) | Ramp Time (min) |
|---|---|---|---|
| 0.0 | 100 | 0.0 | — |
| 19.0 | 100 | 0.0 | 0.5 |
| 19.5 | 0.0 | 100 | — |
| 24.5 | 0.0 | 100 | 0.5 |
| 25.0 | 100 | 0.0 | — |
| 30.0 | 100 | 0.0 | — |

Example 3

Standards, Controls, Calibration, and System Suitability

Galactose concentration was quantitated in reference to known amounts of a 10 mM galactose standard (BioAssay Systems, EGAL-100) that was serially diluted in a linear range from 8 pmol to 1.5 nmol. During method development, a single injection of each point was run prior to sample injections to ensure column and system performance. See FIG. 6.

The monosaccharide 2-deoxy-D-ribose (deoxyribose) was used as an internal standard. An equivalent amount of deoxyribose was added to all protein samples, standards, and controls to monitor electrode performance. Due to the nature of PAD, the internal standard was used to correct for differences in the detector response, which may occur from injection to injection. The area of the galactose peak for all samples was corrected by dividing the galactose area by the deoxyribose area.

A positive control was used to ensure the accuracy of the assay each time it was performed. This required to monitor enzyme function and ensure proper sample handling. The control reaction was a 1 to 1 mixture of commercially available bovine sialylated fetuin and asialo fetuin standard (Sigma F3004 and A4781, respectively). Individually, the sialylated fetuin has a capping percentage of over 99% and the asialo fetuin has a capping percent of 0%. When mixed in equal proportions, the capping (sialylation) ratio for fetuin should be 50%±3%. The fetuin control was prepared as a large batch that was aliquoted, frozen at −70° C., and an individual sample thawed and used as a control each time a set of samples was digested and run using the methods described herein.

A system suitability experiment to ensure performance of the analytical method was monitored using a mixture of galactose and deoxyribose that was injected at the beginning of a run, and bracketed every 12 sample injections (i.e., 2 samples in duplicates), and at the end of the run to monitor electrode and column performance throughout the run. The series of experiments for a typical chromatographic run is shown in Table 4.

TABLE 4

Typical Chromatography Run Sequence

| Sample | Content | Repetition | Injection Volume (μL) |
|---|---|---|---|
| 1 | Buffer Blank[a] | 3 | 20 |
| 2 | High Conc. Std-System Suitability | 3 | 20 |
| 3 | Low Conc. Std[b] | 1 | 20 |
| 4 | High Conc. Std[b] | 1 | 20 |
| 5 | Enzyme Blank[c] | 1 | 20 |
| 6 | Fetuin-Reaction B[d] | 1 | 20 |
| 7 | Fetuin-Reaction C[d] | 1 | 20 |
| 8 | Fetuin-Reaction B[d] | 1 | 20 |
| 9 | Fetuin-Reaction C[d] | 1 | 20 |
| 10 | High Conc. Std-System Suitability[b] | 1 | 20 |
| 11 | Buffer Blank[a] | 1 | 20 |
| 12 | Sample 1-Reaction A | 1 | 20 |
| 13 | Sample 1-Reaction B | 1 | 20 |
| 14 | Sample 1-Reaction C | 1 | 20 |
| 15 | Sample 1-Reaction A | 1 | 20 |
| 16 | Sample 1-Reaction B | 1 | 20 |
| 17 | Sample 1-Reaction C | 1 | 20 |
| 18 | Buffer Blank[a] | 1 | 20 |
| 19 | Sample 2-Reaction A | 1 | 20 |
| 20 | Sample 2-Reaction B | 1 | 20 |
| 21 | Sample 2-Reaction C | 1 | 20 |
| 22 | Sample 2-Reaction A | 1 | 20 |
| 23 | Sample 2-Reaction B | 1 | 20 |
| 24 | Sample 2-Reaction C | 1 | 20 |
| 25 | High Conc. Std-System Suitability[b] | 1 | 20 |
| 26 | Buffer Blank[a] | 1 | 20 |
| N... | N... | 1 | 20 |
| N + 1 | High Conc. Std-System Suitability[b] | 3 | 20 |
| N + 2 | Flush | — | — |

[a]The Buffer Blank was an injection with no material (i.e., contains the A mobile phase only). Additional blank injections may be required to ensure that the column is clean and equilibrated. It is recommended that the second blank injection be used to assess the column cleanliness. A blank injection should also be performed at least once for every 6 sample injections or sooner if necessary (Buffer Blank).
[b]The Low Concentration Standard was 8 pmol galactose and the High Concentration Standard was 1500 pmol galactose. These assay standards were intended to ensure that the sample results were within the linear range of the lowest and highest concentrations for the assay. The 1500 pmol assay control was also used as a system suitability control (e.g., High Concentration Standard-System Suitability) throughout the run to monitor electrode and column performance and should be bracketed each 12-sample injection runs (i.e., four A, B, and C sample sets).
[c]The Enzyme Blank was an injection containing the enzymes (i.e., β-galactosidase and α-sialidase) and buffers without a protein sample (i.e., Reaction C without a protein analyte).
[d]Bovine fetuin (a 1:1 mixture of sialylated and asialo fetuin) was used as a positive control for sialylation.

Example 4

Correction and Calculation of Results

Figure 2:
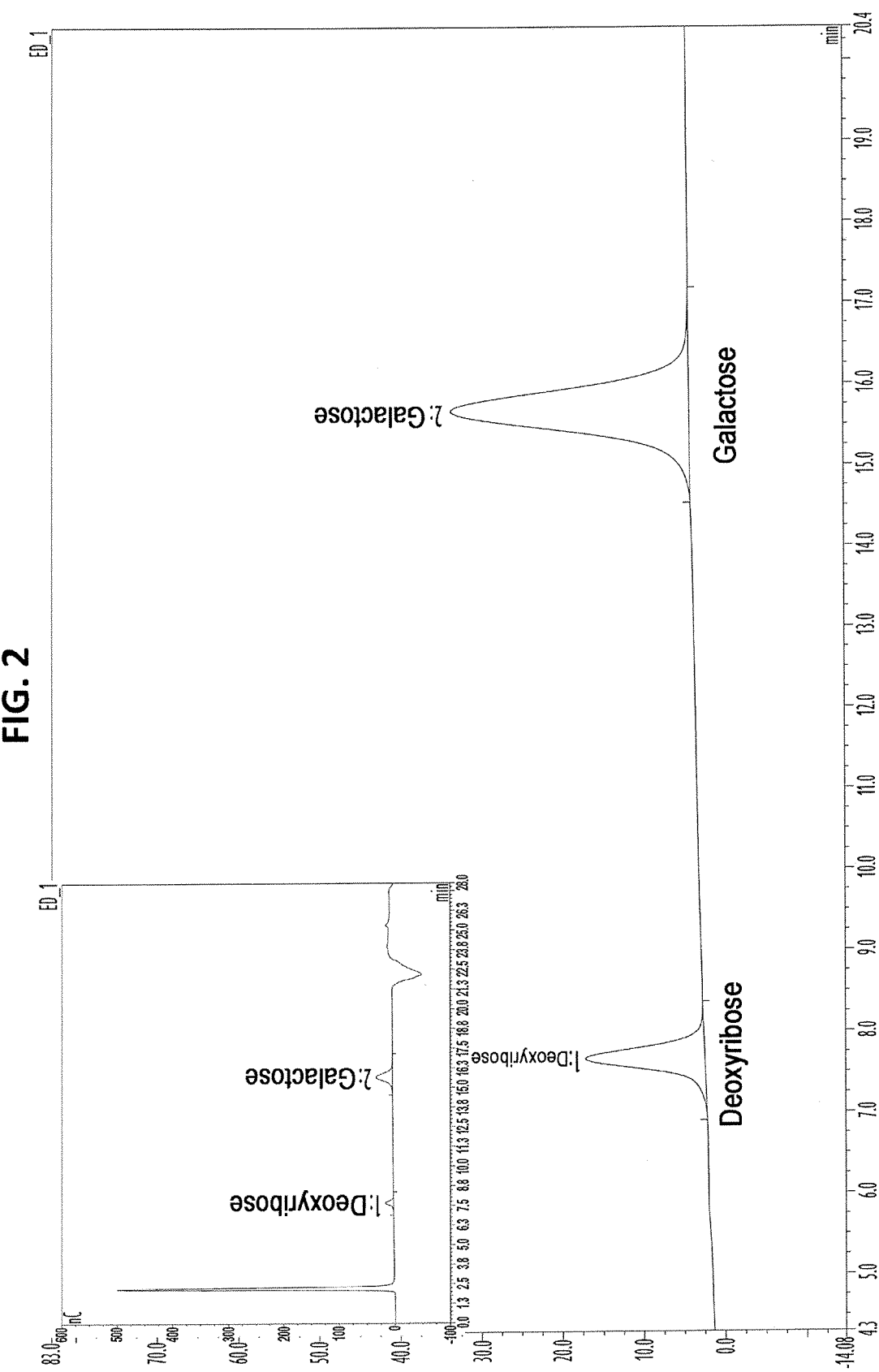
FIG. 2 shows a typical chromatogram for a digested recAlpha-1 sample in Reaction C. Elution times for galactose range from approximately 14 to 16 minutes.

A representative chromatogram is shown in FIG. 2. The areas of all sample injections were corrected by the area of deoxyribose. Corrections were performed by dividing the area of the galactose peak by the area of the deoxyribose peak. This corrected number was then used to calculate percent sialylation. To calculate this percentage, the ratio of uncapped galactose to total galactose was determined using Equation 1:

$$\text{Percent Capping (\%)} = \frac{\text{Reaction } C \text{ (Total Gal)} - \text{Reaction } B \text{ (Uncapped Gal)}}{\text{Reaction } C \text{ (Total Gal)} - \text{Reaction } A \text{ (Gal in media)}} \times 100$$

To calculate the percent capping, the galactose area was divided by the deoxyribose area to give corrected galactose areas. The percent capping was calculated for each of the duplicate injections of a sample using the corrected areas. The corrected galactose area measured for Reaction B was subtracted from the corrected galactose area determined from Reaction C; this value corresponds to the amount of sialyl-capped galactose. The corrected galactose area determined for Reaction A was then subtracted from the corrected galactose area measured for Reaction C; this value corresponds to total galactose (i.e., capped and uncapped). The capped galactose (C−B) was divided by the total galactose (C−A) and multiplied by 100 to give the percentage of sialyl-capping. Representative data are shown in Table 5.

TABLE 5

Representative Galactose Capping Data

| Sample | Deoxyribose Area (nC × min) | Galactose Area (nC × min) | Corrected Area (nC × min) | Percent Capping | Average Percent Capping |
|---|---|---|---|---|---|
| Sample 1 - Reaction A | 4.597 | 0.162 | 0.035 | 97.9 | 97.8 |
| Sample 1 - Reaction B | 4.523 | 0.537 | 0.119 | | |
| Sample 1 - Reaction C | 4.461 | 17.545 | 3.933 | | |
| Sample 1 - Reaction A | 4.723 | 0.150 | 0.032 | 97.7 | |
| Sample 1 - Reaction B | 4.633 | 0.548 | 0.118 | | |
| Sample 1 - Reaction C | 4.557 | 17.48 | 3.763 | | |

The system suitability was monitored using a mixture of galactose and deoxyribose that was injected at the beginning of a run and at the end of the run to monitor electrode and column performance throughout the run. The reported average percent capping was determined from the corrected areas from duplicate injections. If the galactose peak area in Reaction B was less than the galactose peak area in the 8 pmol standard, then percent capping was reported as ">[capping] %" (i.e., "greater than") calculated based on the galactose peak area of the 8 pmol standard in the numerator of the calculation. The calculation of the tailing factor (called "asymmetry" in the Chromeleon® software), theoretical plates, and resolution were performed and determined by the Dionex data acquisition software. The calculations for remaining system suitability criteria were determined manually. Representative system suitability parameters are shown in Table 6.

TABLE 6

Representative System Suitability Parameter Calculations

| Sample | Deoxyribose Asymmetry | Deoxyribose Resolution | Deoxyribose Theoretical Plates | Deoxyribose Retention Time (min) | Deoxyribose Area (nC × min) | Galactose Area (nC × min) | % Difference Deoxyribose Retention Time | % Difference Galactose Area |
|---|---|---|---|---|---|---|---|---|
| Suitability | 0.92 | 10.20 | 3281 | 7.62 | 7.210 | 38.735 | 0 | −3 |
| Suitability | 0.92 | 10.25 | 3323 | 7.62 | 6.846 | 36.872 | 0 | −8 |
| Suitability | 0.94 | 10.28 | 3330 | 7.62 | 7.242 | 39.057 | 0 | −2 |
| 1500 pmol | 0.93 | 10.29 | 3334 | 7.62 | 7.410 | 39.749 | 0 | — |
| 8 pmol | 0.92 | 11.36 | 3337 | 7.62 | 7.595 | 0.215 | 0 | — |
| RAD6425 A | 0.92 | — | 3377 | 7.60 | 7.377 | — | 0 | — |
| RAD6425 B | 0.93 | 11.26 | 3308 | 7.57 | 7.031 | 0.236 | −1 | — |
| RAD6425 C | 0.91 | 10.27 | 3276 | 7.57 | 6.863 | 12.407 | −1 | — |
| RAD6425 A | 0.93 | — | 3304 | 7.57 | 6.631 | — | −1 | — |
| RAD6425 B | 0.91 | 11.45 | 3301 | 7.57 | 7.228 | 0.229 | −1 | — |
| RAD6425 C | 0.90 | 10.24 | 3283 | 7.57 | 7.107 | 12.833 | −1 | — |
| Suitability | 0.93 | 10.18 | 3298 | 7.58 | 7.330 | 39.516 | 0 | −1 |
| Suitability | 0.93 | 10.27 | 3326 | 7.60 | 7.345 | 39.758 | 0 | 0 |
| Suitability | 0.92 | 10.25 | 3345 | 7.62 | 7.220 | 39.041 | 0 | −2 |

System suitability assay acceptance criteria are shown in Table 7.

TABLE 7

System Suitability Assay Acceptance Criteria

| Parameters for System Suitability | Criteria |
|---|---|
| Percent difference of retention time of deoxyribose in the sample relative to the retention time of deoxyribose in the average of the high and low concentration standard | ±5% |
| Percent difference of galactose area of initial assay control (high concentration standard) and bracketing assay control injections (i.e., high concentration standard system suitability injections) | ±15% |
| Percent difference of the % capping of the duplicate recAlpha-1 samples | ±2% |
| Percent difference of the control % capping result from the previously established and expected % capping result. | ±3% of established value |
| Tailing Factor (i.e., Asymmetry)* | 1 ± 0.2 |
| Theoretical Plates* | ≥2000 |
| Resolution* | ≥8.5 |

*The Tailing Factor was determined using the deoxyribose peak for each sample injection.

Example 5

Stoichiometry of Sample/Enzymatic Reactions and Digestion Time

In order to optimize the enzyme reaction rate, the ratio of enzyme to protein was analyzed. The β-galactosidase enzyme is provided by the manufacturer at an activity of >3 Units/mL (specific activity >6 Units/mg), while α-Sialidase enzyme has an activity of 5 Units/mL (specific activity at 135 Units/mg). The amount of each enzyme was held constant at 4 μL each, corresponding to 0.012 Units of β-galactosidase and 0.02 Units of α-sialidase in the reaction, while the protein amount was varied from 540 to 2160 pmol. The samples analyzed were a buffer-exchanged and filtered recAlpha-1 in cell culture supernatant at a concentration of 1.4 mg/mL. The samples were prepared for as shown in Table 8.

TABLE 8

Reaction Stoichiometry

| Sample RAD0906 Volume (μL) | Reaction Volume (μL) | Sample Concentration After Reaction Addition (mg/mL) |
|---|---|---|
| 20 | 20 | 0.7 |
| 40 | 20 | 0.9 |
| 80 | 20 | 1.1 |

For each recAlpha-1 reaction stoichiometry and digestion time point, the galactose chromatographic peak area was analyzed and the percent capping was determined. A summary of results are shown in Table 9, which demonstrate that capping value does not change for any of the stoichiometric conditions. The original reaction stoichiometry (e.g., 2.2× $10^{-5}$ Units/pmol protein) was estimated based on the manufacturer's recommendations. However, these results indicate that the enzymes may be excessive at the vendor recommended conditions, even when the protein concentration was increased by 4-fold. Given this wide dynamic range of stoichiometry, a "mid-point" stoichiometric condition (i.e., approximately 1.1×$10^{-5}$ Units/pmol protein) was chosen in order to simplify the procedure, minimize enzyme cost, and allow sufficient robustness in sample preparation.

TABLE 9 recAlpha-1 Reaction Stoichiometry Results

| Protein (pmol) | Protein Volume (μL) | Sample Type | β-galactosidase (units) | Sialidase (units) | β-galactosidase (units/pmol) | Sialidase (units/pmol) | Galactose Area (nC × min) | % Capping |
|---|---|---|---|---|---|---|---|---|
| 540 | 20 | B | 0.012 | — | $2.22 \times 10^{-5}$ | — | 0.710 | 96.6 |
| 540 | 20 | C | 0.012 | 0.02 | $2.22 \times 10^{-5}$ | $3.7 \times 10^{-5}$ | 21.78 | 96.6 |

TABLE 9-continued recAlpha-1 Reaction Stoichiometry Results

| Protein (pmol) | Protein Volume (µL) | Sample Type | β-galactosidase (units) | Sialidase (units) | β-galactosidase (units/pmol) | Sialidase (units/pmol) | Galactose Area (nC × min) | % Capping |
|---|---|---|---|---|---|---|---|---|
| 1080 | 40 | B | 0.012 | — | $1.11 \times 10^{-5}$ | — | 0.740 | 96.4 |
| 1080 | 40 | C | 0.012 | 0.02 | $1.11 \times 10^{-5}$ | $1.8 \times 10^{-5}$ | 18.817 | 96.4 |
| 1080 | 40 | B | 0.012 | — | $1.11 \times 10^{-5}$ | — | 0.638 | 96.6 |
| 1080 | 40 | C | 0.012 | 0.02 | $1.11 \times 10^{-5}$ | $1.8 \times 10^{-5}$ | 18.817 | 96.6 |
| 1080 | 40 | B | 0.012 | — | $1.11 \times 10^{-5}$ | — | 0.647 | 96.8 |
| 1080 | 40 | C | 0.012 | 0.02 | $1.11 \times 10^{-5}$ | $1.8 \times 10^{-5}$ | 20.323 | 96.8 |
| 2160 | 80 | B | 0.012 | — | $5.56 \times 10^{-6}$ | — | 0.565 | 96.7 |
| 2160 | 80 | C | 0.012 | 0.02 | $5.56 \times 10^{-6}$ | $9.1 \times 10^{-6}$ | 17.204 | 96.7 |
| | | | | | | | Average | 96.6 |
| | | | | | | | Std Dev. | 0.15 |
| | | | | | | | % RSD | 0.16 |

Reaction stoichiometry was also examined by comparing the capping results for an upstream recAlpha-1 sample (RAD-0637) prepared on Day 1 using 4 µL of enzyme in the reaction and on Day 2 (14 days later), using 2 µL of enzyme. Results of the experiment show the same capping value for the 2 µL and 4 µL enzyme amounts indicating that 2 µL of enzyme was sufficient for the reaction to proceed to completion, consistent with the above observation (Table 10).

TABLE 10

Enzyme Quantity Results

| Analysis Date | Enzyme volume (µL) | Percent Capping |
|---|---|---|
| Day 1 | 4 | 97.4 |
| Day 2 | 2 | 97.2 |

Example 6

Internal Standard

In this HPAEC-PAD method, an internal standard was used to normalize the peak area of the galactose due to the inherent variability of the amperometric detection in each injection. Initially, two internal standards were tested: galactosamine and deoxyribose. Both internal standards functioned adequately and both eluted at times sufficiently different from galactose and did not interfere with quantitation. Although galactosamine performed adequately, some inconsistencies in peak areas were observed that would require broader acceptance criteria to monitor system performance. Consequently, deoxyribose was selected as the internal standard. Further, deoxyribose is commonly used as an industry standard for amperometric detection methods. Areas for the deoxyribose peak showed less variability throughout the long injection sequences and could be used under tighter acceptance criteria.

During development, several instances of unexplained increases or decreases in deoxyribose area were observed. However, in these same samples, an increase or decrease in the deoxyribose area was followed by the opposite change in the galactose peak (Table 11).

TABLE 11

Changes in Observed Deoxyribose Peak Area

| Sample Name | Deoxyribose Area (nC × min) | Galactose Area (nC × min) |
|---|---|---|
| Fetuin, Reaction B | 3.724 | 11.858 |
| Fetuin, Reaction C | 3.940 | 25.019 |
| Fetuin, Reaction B | 5.482 | 8.363 |
| Fetuin, Reaction C | 5.179 | 17.452 |
| RAD6236, Reaction A | 3.855 | 0.082 |
| RAD6236, Reaction B | 3.885 | 0.548 |
| RAD6236, Reaction C | 3.991 | 11.560 |
| RAD6236, Reaction A | 4.589 | 0.089 |
| RAD6236, Reaction B | 4.483 | 0.406 |
| RAD6236, Reaction C | 4.540 | 10.227 |

Typically, fluctuations in peak area could be explained as differences in response by the electrode. If this were the case, both peaks would be expected to increase or decrease. An experiment was performed where deoxyribose was added to three samples but not mixed. The samples were analyzed by HPAEC-PAD, then removed and vortexed to ensure mixing of sample and internal standard. The samples were then re-injected. The results of these experiments show that the fluctuation in areas results from insufficient mixing of the sample and the internal standard. This suggests that stratification between the internal standard solution and sample can occur and users must mix the reaction sufficiently before placing on autosampler tray. The results from these experiments are summarized in Table 12.

TABLE 12

Confirmation of Insufficient Mixing Causing Deoxyribose Peak Area Fluctuations

| Sample | Preparation | Deoxyribose Area (nC × min) | Galactose Area (nC × min) |
|---|---|---|---|
| RAD6249 Reaction C | No mixing | 3.172 | 22.260 |
| Fetuin Reaction C | No mixing | 2.460 | 17.247 |
| 2C9 Reaction C | No mixing | 2.762 | 18.110 |
| RAD6249 Reaction C | After mixing | 4.704 | 17.607 |
| Fetuin Reaction C | After mixing | 4.933 | 12.440 |
| 2C9 Reaction C | After mixing | 4.877 | 14.671 |

Example 7

Enzyme Vendor Comparison

Given the criticality of the β-galactosidase and sialidase enzyme quality to the reaction rate and galactose quantitation, four different vendor's β-Galactosidase and α-sialidase enzymes were compared. The objective was to gauge the adequacy of the reaction rate that would provide an accurate response and to establish a back-up vendor in case the primary vendor's enzymes were no longer commercially available. The vendors selected were Sigma, Glyko-Prozyme, New England BioLabs, and QA Bio. QA Bio enzymes were used for the majority of the experiments described herein. Sigma was eliminated when an enzyme reaction did not yield a response. Glyko-Prozyme was also eliminated as an option when the galactose peak areas were the same for samples treated with β-galactosidase as those samples treated with both β-galactosidase and α-sialidase in two separate experiments (i.e., the α-sialidase activity was nondetectable). Head-to-head experiments comparing New England BioLabs and QA Bio enzymes were prepared and run on the same day. The results were also compared to data from previous days with the same samples digested with QA Bio enzymes. The percent differences between the two enzymes was negligible and the relative standard deviation (% RSD) for the several trial runs indicated that New England BioLabs β-Galactosidase and α-sialidase enzymes were comparable to QA Bio and could be used as a back-up vendor in case the QA Bio enzymes were no longer commercially available. The experimental results are summarized in Table 13.

TABLE 13

Results of Samples Digested using QA Bio or New England BioLabs Enzymes

| Sample | Analysis Date | Enzyme Manufacturer | Percent Capping |
|---|---|---|---|
| Fetuin | Day 1 | QA Bio | 49.5 |
| Fetuin | Day 5 | QA Bio | 52.1 |
| Fetuin | Day 5 | New England BioLabs | 52.8 |
|  |  | Average | 51.5 |
|  |  | Std Dev. | 1.74 |
|  |  | % RSD | 3.38 |
| RAD0637 | Day 1 | QA Bio | 97.4 |
| RAD0637 | Day 15 | QA Bio | 97.2 |
| RAD0637 | Day 15 | New England BioLabs | 97.6 |
|  |  | Average | 97.4 |
|  |  | Std Dev. | 0.20 |
|  |  | % RSD | 0.21 |

Example 8

Sample Type and Preparation

Given that upstream protein samples can contain 5 mg/mL galactose from cell culture media, a sample preparation method was developed to remove the majority of the excess galactose from the media, as well as other potentially interfering excipients. This clean up alone was not sufficient to remove all process impurities, so additional clean up must be performed as part of the capping method preparation. Two methods of rapid clean-up were evaluated: dialysis against deionized water and 10 kDa centrifugal spin filtering.

Figure 3:
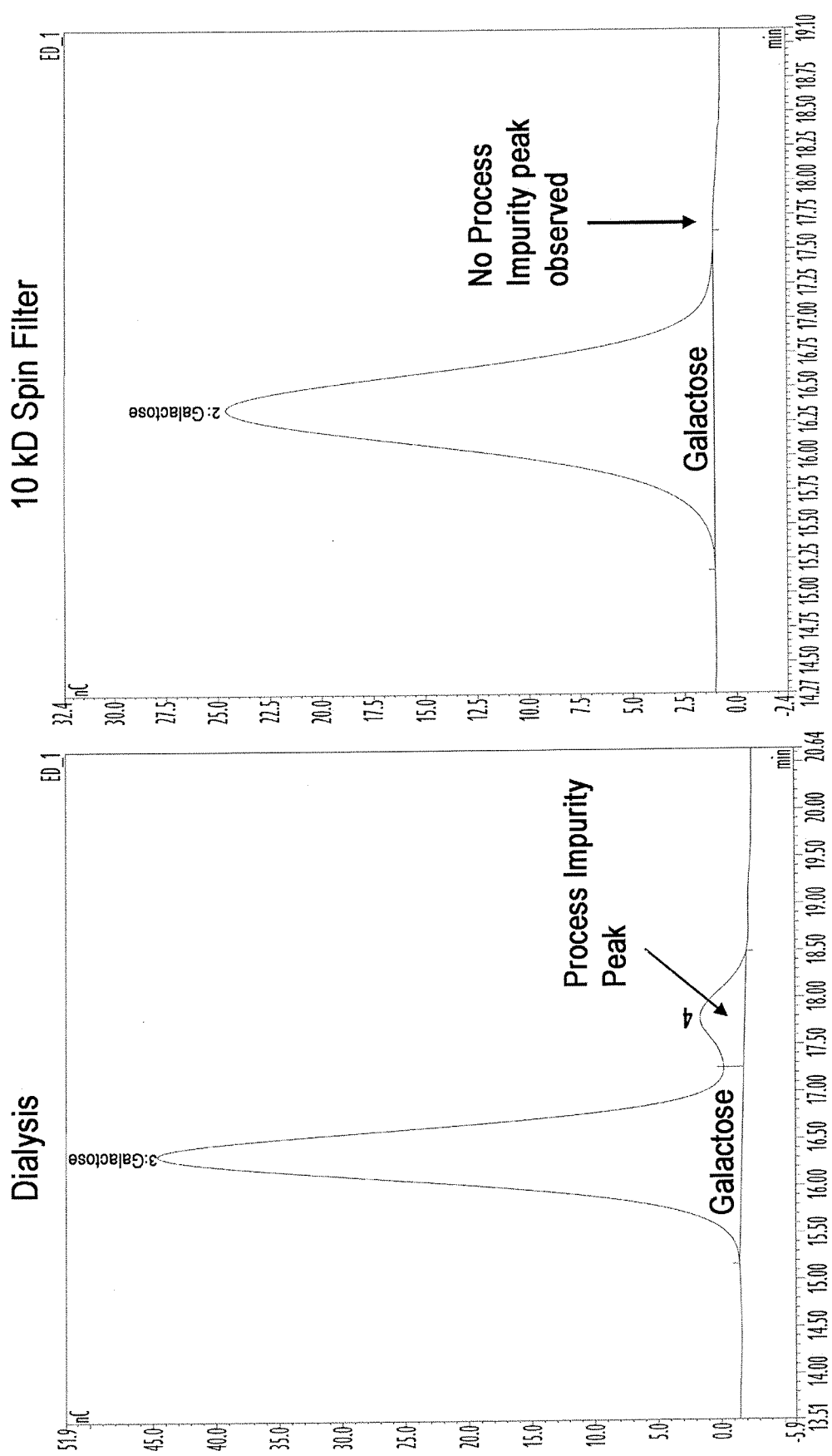
FIG. 3 shows a comparison of an upstream recAlpha-1 sample that was either dialyzed against deionized water or centrifuged in a 10 kDa spin filter. Impurities remained in the dialyzed sample, but were almost totally removed by the 10 kDa spin filter.

The experiment utilized a buffer-exchanged recAlpha-1 sample. In this experiment, a sample was dialyzed against deionized water for 4 hours while another sample was simultaneously cleaned using a 10 kDa spin filter. Both samples were then analyzed by the capping method. The conclusion from the experiment was that the 10 kDa spin filters were more effective at removing impurities than dialysis and allow for preparation of up to 30 samples at once, at a significantly increased turnaround time. The chromatograms of both cleanup procedures that involved digestion with Reaction C (β-galactosidase and α-sialidase) are shown in FIG. 3. The spin filtered sample was reconstituted with deionized water and consequently has a lower concentration than the dialyzed sample. Although trace amounts of galactose may still be present after the clean-up, all background peaks (i.e., Reaction A) were subsequently accounted for in the percent capping calculation by subtracting out the contaminate peak area.

Figure 4:
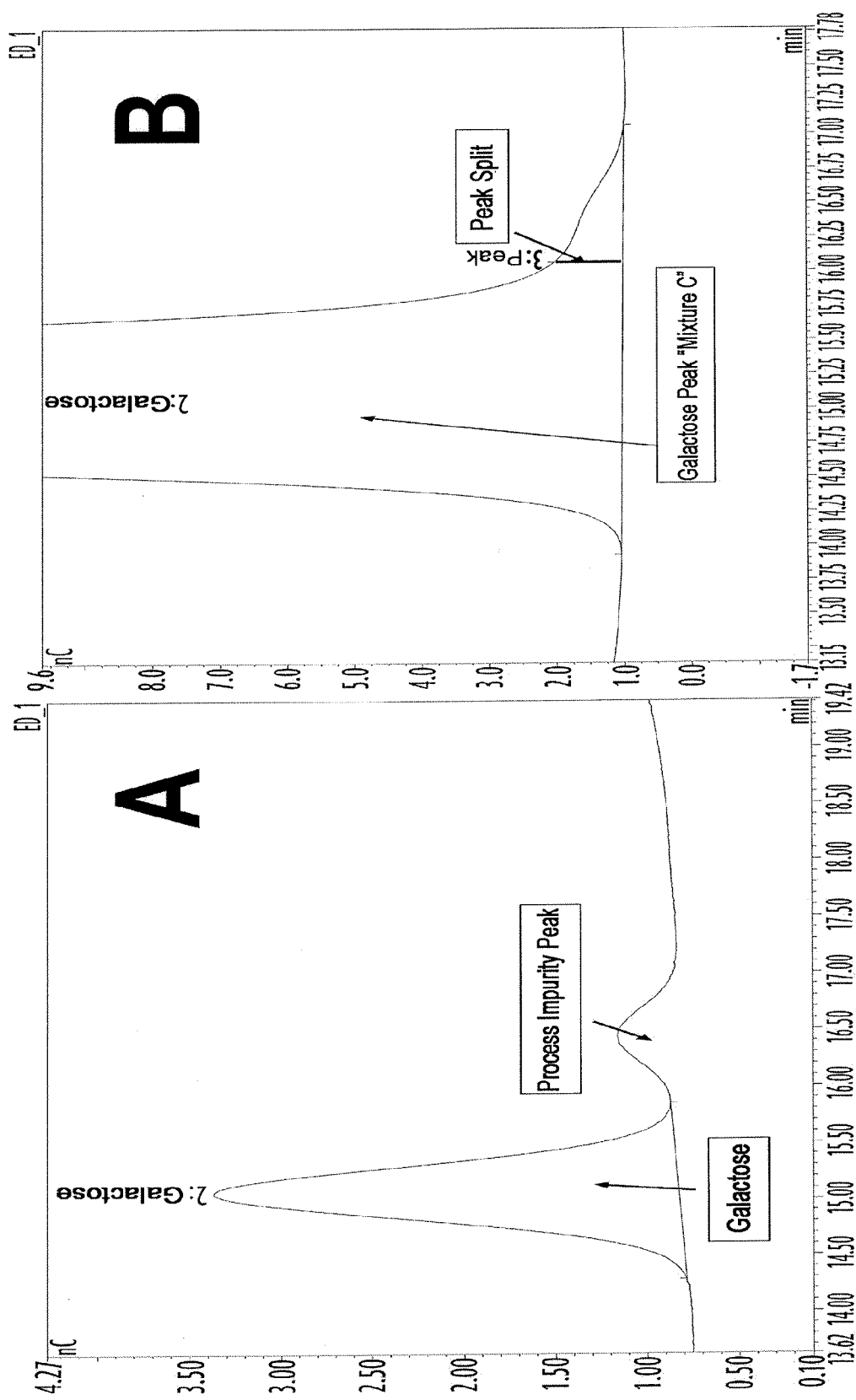
FIG. 4 demonstrates that upstream excipients from recAlpha-1 culture media can be detected and may co-elute near the galactose peak. In panel A, an excipient peak is shown which elutes next to galactose peak in some samples after spin filter clean up. For Reaction B samples, the impurity peak is baseline resolved from the galactose peak and is not integrated. In panel B, the process impurity peak co-elutes with a Reaction C sample. In this case, the impurity peak must be split as shown above to exclude it from being integrated with the area of the galactose peak.

It was also observed that some excipient(s) from the cell culture supernatants elute shortly after the galactose peak, and in some cases, appear as a peak shoulder on the galactose peak (see FIG. 4). In such cases where certain residual excipients cannot be removed by the 10 kDa spin filter, the presence of this impurity was excluded from the galactose peak area of by performing "drop down" integration and not integrating the impurity peak.

Example 9

Specificity

Figure 5:
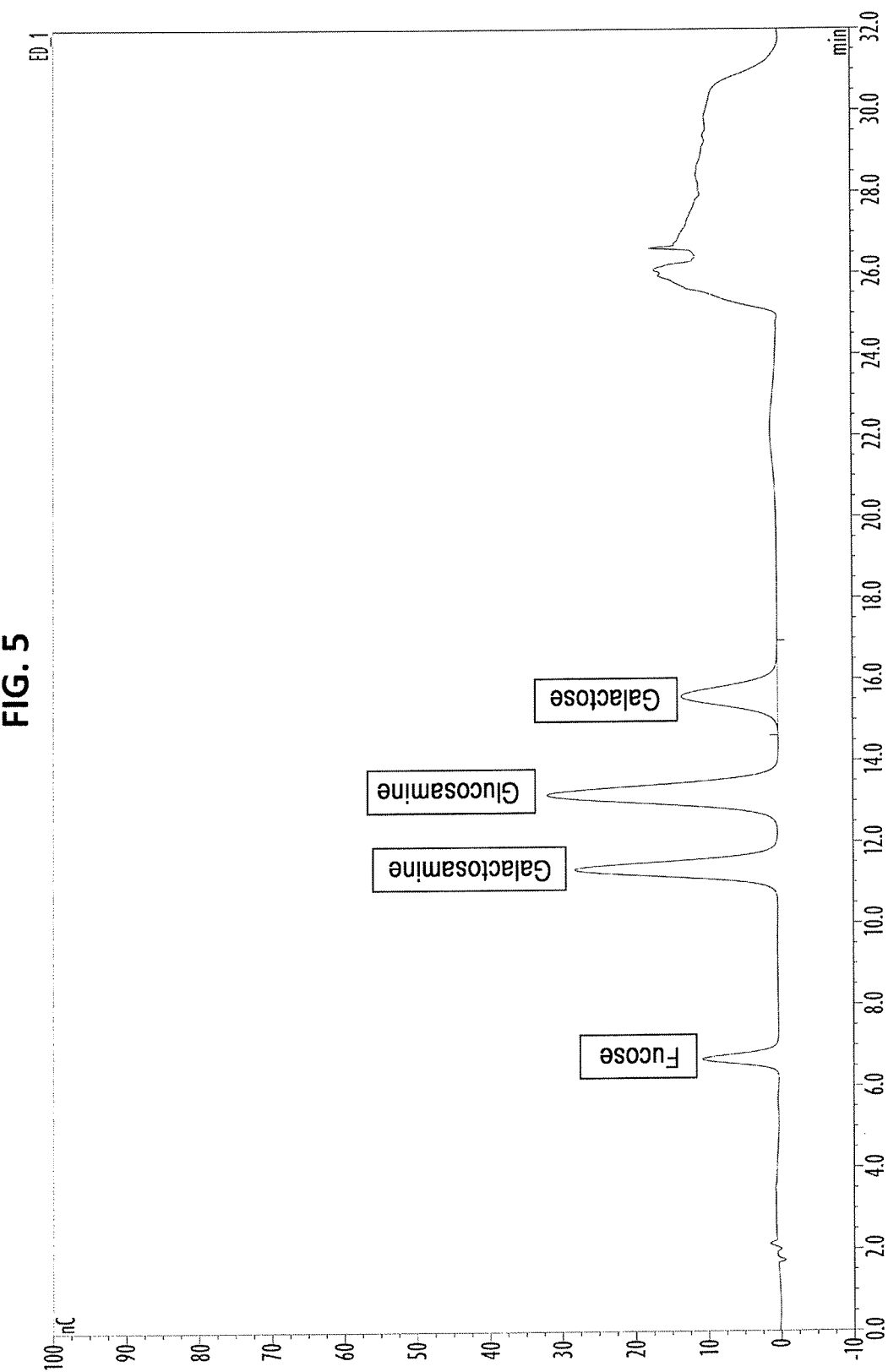
FIG. 5. Method specificity was confirmed by analyzing a mixture of neutral and amino monosaccharides derived from glycoproteins.

Specificity is the ability of the method to assess the analyte in the presence of components that may be expected to be present, such as impurities, degradation products, matrices, etc. The specificity of the method was determined by preparing a mixture of commercially available neutral and amino monosaccharides and analyzing the mixture by HPAEC-PAD. The sugars evaluated were fucose, galactosamine, glucosamine, and galactose. The sugars were analyzed individually to confirm retention times, and then analyzed as a mixture to determine specificity (FIG. 5). The separation of monosaccharides was comparable to that seen in Dionex Technical Note 20, where galactose elutes after all three other monosaccharides. See Dionex Technical Note 20, Analysis of Carbohydrates by High Performance Anion Exchange Chromatography with Pulsed Amperometric Detection (HPAE-PAD), Dionex Corp. (2000). In addition, for highly impure samples, i.e., cell culture supernatants, the background levels were analyzed to evaluate whether any interfering excipients were present and whether they were removed through sample preparation.

Example 10

Linearity

Figure 6:
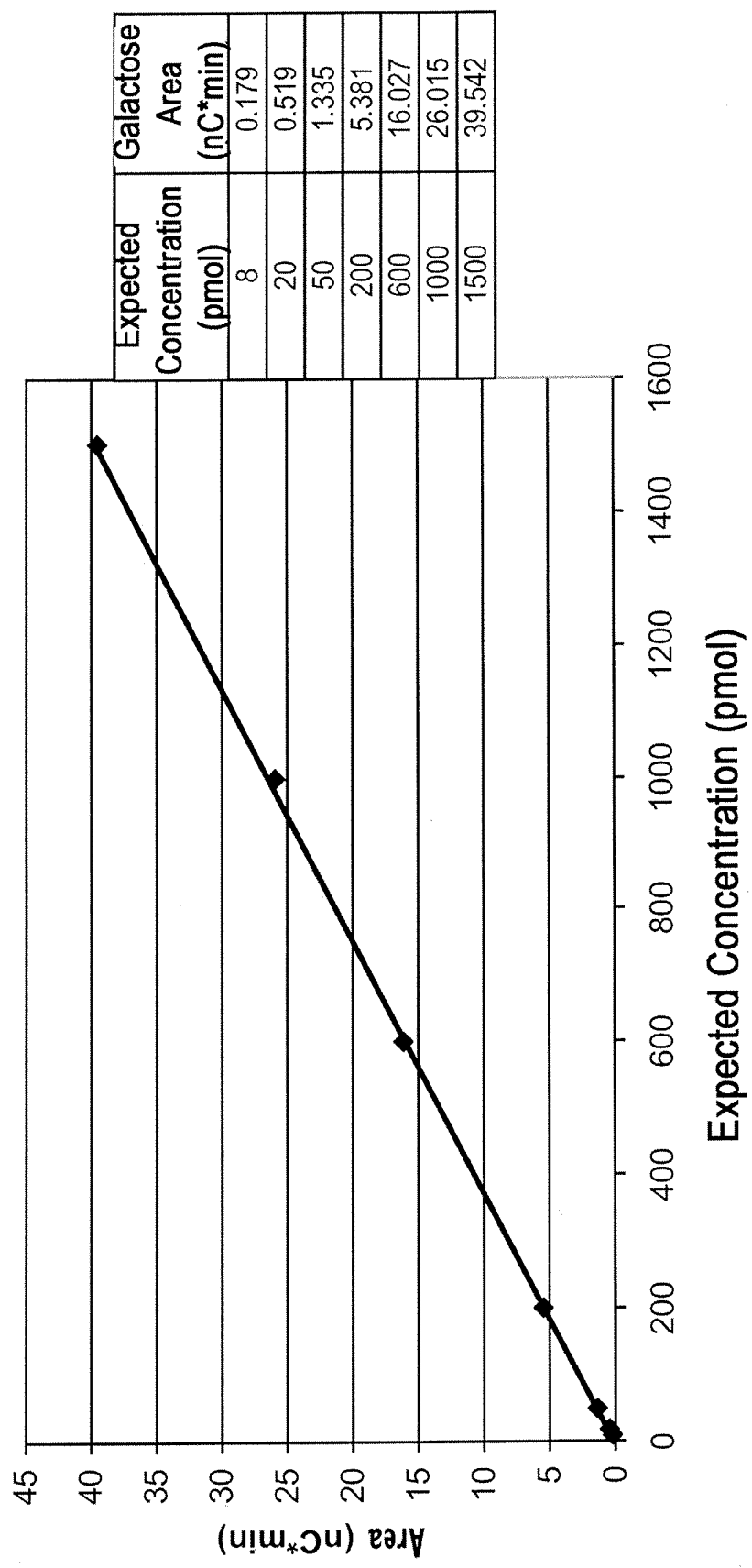
FIG. 6. Example of a typical galactose standard curve.

The linearity of the HPAEC PAD sialylation assay is its ability to obtain test results that are directly proportional to the analyte concentration or content within a given range. In addition, a range derived from the linearity study was used to confirm the acceptable degree of linearity, accuracy, and precision attainable by the procedure. The linearity for the method was evaluated by preparing a galactose standard calibration curve with an optimal range from 8 pmol to 1.5 nmol (FIG. 6). The coefficient of determination (regression coefficient) was 0.99 or greater for the 8 pmol to 1.5 nmol range. The regression residuals were also analyzed and shown not to be biased in that range. The calibration curve can be extended up to 2 nmol and maintain acceptable linearity, but with a loss of accuracy at the low end of the calibration curve. The optimal calibration curve range was monitored over different dates, using different systems, columns, and Dionex ICS-3000 disposable gold electrodes. Table 14 summarizes these results.

TABLE 14

Summary of R-squared, Slope, and y-intercept for Six Calibration Curves

| Analysis Date | Instrument | $R^2$ | Slope | y-intercept |
|---|---|---|---|---|
| Day 1 | RTQ-0087 | 0.9999 | 0.0276 | 0.0435 |
| Day 4 | RTQ-0094 | 1.0000 | 0.0279 | −0.0139 |
| Day 11 | RTQ-0094 | 0.9999 | 0.0263 | 0.0342 |
| Day 39 | RTQ-0094 | 1.0000 | 0.028 | 0.0029 |
| Day 42 | RTQ-0094 | 1.0000 | 0.0308 | −0.0553 |
| Day 46 | RTQ-0087 | 0.9998 | 0.0297 | 0.1138 |

Example 11

Limit of Quantitation

The limit of quantitation (LOQ) of the HPAEC PAD sialylation assay indicates the lowest amount of analyte in a sample that can be determined quantitatively with suitable precision and accuracy. There are several ways to calculate the LOQ of a quantitative method. One method is based on the standard deviation of γ-intercept divided by the average slope. Another method is based on visual analysis of the chromatogram. First, the LOQ of the assay was calculated based on the signal-to-noise ratio of a typical chromatogram. Specifically, the noise level in a 1-minute horizontal region of the chromatogram was measured and multiplied by 10 to yield the LOQ in terms of peak height. The peak height was then converted to the pmol amounts based on the peak height of the calibration standards. The noise level results were compared to a calibration standard that yielded similar response (see Table 15). The noise level was obtained over six different days on two different ICS-3000 systems. These results indicate that the noise levels on different days gave similar results (±0.02) and were at approximately the 8 pmol standard level (difference of 0.12 nC×min, which was insignificant compared to the height of the 1500 pmol standard at approximately 70 nC×min).

TABLE 15

Comparison of Noise Level Over Six Analyses for 8 pmol Galactose

| Analysis Date | Instrument | Noise Level Difference × 10 (nC × min) | Standard Peak Height 8 pmol galactose |
|---|---|---|---|
| Day 1 | RTQ-0094 | 0.22 | 0.27 |
| Day 7 | RTQ-0087 | 0.25 | 0.40 |
| Day 14 | RTQ-0087 | 0.27 | 0.37 |
| Day 28 | RTQ-0087 | 0.22 | 0.36 |
| Day 36 | RTQ-0087 | 0.25 | 0.30 |
| Day 37 | RTQ-0087 | 0.23 | 0.45 |
| | Average | 0.24 | 0.36 |

Because the chromatogram noise level may change from instrument to instrument, the LOQ was also calculated in a different manner. Based on the values in Table 14 and specifically on the standard deviation of the γ-intercept (0.0577) divided by the average slope (0.0283) and multiplied by 10, the LOQ was calculated to be 20 pmol. The two methods of calculating the limit of quantitation suggest that LOQ was approximately 8 to 20 pmol.

Example 12

Method Accuracy

The accuracy of the method was determined by the agreement between a known standard and the experimentally-measured results. Because there is no "gold standard" to serve as a reference, the accuracy of the method was determined using an equal mixture of commercially available sialylated and asialo fetuin standards. The sialylated bovine fetuin standard and the asialo fetuin standard were prepared in equal concentrations as determined by UV absorbance at 280 nm (i.e., $A_{280}$). The standards were analyzed individually, then prepared in a 1:1 ratio and analyzed. The sialylated fetuin standard had a percent capping of 99.4% while the asialo fetuin standard had a percent capping result of 1.2%, due to the amount of galactose in the Reaction B being slightly higher than Reaction C. Based on these findings, the expected capping percentage for the fetuin mix control would be approximately 50%. The actual result for the fetuin mixture was established to be 49.3% based on the average of multiple runs. Results for the experiment are summarized in Table 16. Although the exact derivation of the variability or accuracy stemming from the $A_{280}$ measurement cannot be made, these results indicate that this method was accurate to within a few percentage points. Furthermore, this fetuin control was analyzed as part of the intermediate precision studies on different days (see Table 18 and Table 19, below), and was shown to have a relative standard deviation (% RSD) of 3%. The use of such a control is recommended each time the assay is performed.

TABLE 16

Results for Fetuin Standards to Determine Accuracy of the HPAEC-PAD Method

| Fetuin | Reaction | Galactose Area (nC × min) | Percent Capping | Percent Recovery |
|---|---|---|---|---|
| Asialo | A | 0 | −1.2 | 100 |
| Asialo | B | 27.636 | | |
| Asialo | C | 27.301 | | |
| Sialylated | A | 0 | 99.4 | 100 |
| Sialylated | B | 0.182 | | |
| Sialylated | C | 28.808 | | |
| Reaction | A | 0 | 49.3 | 99 |
| Reaction | B | 14.019 | | |
| Reaction | C | 27.657 | | |

Example 13

Reproducibility

The repeatability of the assay was evaluated for the consistency of the results obtained from the method during a short interval of time under the prescribed conditions. The repeatability of the method was determined using a recAlpha-1 cell culture supernatant sample over six replicate injections. The background sample (i.e., Reaction A) was not analyzed because this sample had been previously analyzed and shown not to contain any interfering galactose. The relative standard deviation was determined for galactosamine area, galactose area, and percent capping over the six replicate injections. The results are summarized in Table 17 and are shown both corrected by galactosamine area and without correction. The data shows the repeatability to be about 0.20%.

TABLE 17

Reproducibility of the Method

| Sample Injection No. | Reaction | Area Galactosamine (nC × min) | Galactose Area (nC × min) | Corrected Area (nC × min) | Percent Capping | Percent Capping with out Correction |
|---|---|---|---|---|---|---|
| 1 | B | 14.681 | 1.364 | 0.093 | 96.8 | 96.5 |
| 1 | C | 13.408 | 39.026 | 2.911 | | |
| 2 | B | 14.917 | 1.359 | 0.091 | 96.8 | 96.6 |
| 2 | C | 13.851 | 39.396 | 2.844 | | |
| 3 | B | 14.865 | 1.389 | 0.093 | 96.6 | 96.5 |
| 3 | C | 14.506 | 39.863 | 2.748 | | |
| 4 | B | 15.241 | 1.412 | 0.093 | 96.5 | 96.2 |
| 4 | C | 14.140 | 37.593 | 2.659 | | |
| 5 | B | 14.936 | 1.375 | 0.092 | 96.4 | 96.5 |
| 5 | C | 15.070 | 38.760 | 2.572 | | |
| 6 | B | 14.710 | 1.360 | 0.092 | 96.3 | 96.5 |
| 6 | C | 15.532 | 39.260 | 2.528 | | |
| Average | Gal Only | 14.897 | 1.376 | 0.092 | 96.6 | 96.5 |
| | Gal + Sal | 14.418 | 38.983 | 2.70 | | |
| Std Dev. | Gal Only | 0.201 | 0.021 | 0.001 | 0.19 | 0.11 |
| | Gal + Sal | 0.786 | 0.775 | 0.151 | | |
| % RSD | Gal Only | 1.35 | 1.50 | 0.82 | 0.2 | 0.12 |
| | Gal + Sal | 5.45 | 1.90 | 5.59 | | |

Example 14

Intermediate Precision

In addition to the repeatability study, the intermediate precision analysis incorporated several additional factors: different days, different instrument set-up, and different sample preparation. The intermediate precision of the method was investigated by preparing a downstream process development recAlpha-1 sample (RAD-5904) for capping analysis on three different days and at three different concentrations. For the analyses, different Dionex ICS-3000 chromatography systems, disposable electrodes, amino trap columns, guard columns, and analytical columns were used. The results show the relative standard deviation (RSD) of the sample to be 0.25%. In addition, the capping percentages of the fetuin control prepared over the three analysis days were also compared. The RSD of the fetuin control was 2.99%. Results for intermediate precision of recAlpha-1 samples and fetuin control are summarized in Table 18 and Table 19, respectively. The areas were averaged from duplicate runs and were not corrected.

TABLE 18

Intermediate Precision Results for recAlpha-1

| Sample Volume (µL) | Reaction | Area (nC × min) | Percent Capping |
|---|---|---|---|
| Day 1 | | | |
| 20 | B | 0.525 | 95.7 |
| 20 | C | 12.073 | |
| 40 | B | 0.7035 | 95.5 |
| 40 | C | 15.756 | |
| 80 | B | 0.4335 | 95.4 |
| 80 | C | 9.48 | |
| Day 2 | | | |
| 20 | B | 0.491 | 95.9 |
| 20 | C | 12.0425 | |
| 40 | B | 0.6645 | 95.7 |
| 40 | C | 15.396 | |
| 80 | B | 0.3745 | 96.2 |
| 80 | C | 9.7415 | |
| Day 3 | | | |
| 20 | B | 0.554 | 95.8 |
| 20 | C | 13.161 | |
| 40 | B | 0.708 | 95.9 |
| 40 | C | 17.434 | |
| 80 | B | 0.417 | 95.9 |
| 80 | C | 9.298 | |
| | Average | | 95.7 |
| | Std Dev. | | 0.24 |
| | % RSD | | 0.25 |

TABLE 19

Intermediate Precision results for Fetuin Control

| Fetuin Reaction | Area (nC × min) | Percent Capping |
|---|---|---|
| Day 1 | | |
| B | 14.119 | 51.8 |
| C | 29.281 | |
| Day 2 | | |
| B | 13.679 | 49.3 |
| C | 27.002 | |
| Day 3 | | |
| B | 18.683 | 49.1 |
| C | 36.676 | |
| Average | | 50.1 |
| Std. Dev | | 1.50 |
| % RSD | | 2.99 |

Example 15

Robustness

The robustness of the assay is a measure of its capacity to remain unaffected by small, but deliberate variations in method parameters or sample handling. Several different factors were deliberately varied in a few sets of experiments, such as autosampler stability, enzyme reaction time, enzyme volume, and matrix interference.

Sample Stability in Autosampler

Robustness was determined by examining the sample stability over 48 hours at the HPLC autosampler conditions (i.e., 10° C.) to determine whether the sample awaiting injection in the autosampler at 10° C. would compromise the quality of the results. A singly prepared sample held in the autosampler was injected at various intervals and the peak response of the galactose amounts was determined for each time point. The results are summarized in Table 20 and show a relative standard deviation value of 0.23%, consistent with the relative standard deviation determined from the intermediate precision. Results are shown both corrected by the galactosamine peak area and without correction. These data indicate that samples may be kept on the autosampler for up to 48 hours prior to injection without affecting capping results.

TABLE 20

Results for Sample Stability in Autosampler

|  | Reaction | Galactosamine Area (nC × min) | Galactose Area (nC × min) | Corrected Area (nC × min) | Percent Capping | Corrected Percent Capping |
|---|---|---|---|---|---|---|
| Average | B | 14.465 | 1.353 | 0.094 | 96.4 | 96.4 |
|  | C | 14.601 | 37.900 | 2.600 |  |  |
| Std Dev | B | 0.48 | 0.04 | 0.00 | 0.10 | 0.22 |
|  | C | 0.59 | 1.27 | 0.14 |  |  |
| % RSD | B | 3.35 | 2.69 | 2.19 | 0.10 | 0.23 |
|  | C | 4.01 | 3.34 | 5.28 |  |  |

Enzyme Reaction Time

Robustness was also examined by varying the enzymatic reaction time from 1 to 4 hours to find an explanation for variability in different rates of reaction for different enzyme batches. A sample was incubated at 1, 2.5, and 4 hour time points and each was analyzed. The results are summarized in Table 21 and show that although percent capping was similar for the three reaction times, the one-hour digestion sample was slightly lower than the longer reactions. Based on these data, a 2.5-hour digest was determined to be sufficient for the reaction to run to completion. Given that the method depends on the reaction rate of two enzymes, the lower percent capping results in the 1-hour reaction time indicates that the sialidase enzyme was the rate-limiting step.

TABLE 21

Results for Enzyme Reaction Times

| Sample Volume (µL) | Reaction | Reaction Time (h) | Galactose Area (nC × min) | Percent Capping |
|---|---|---|---|---|
| 40 | B | 1 | 0.740 | 96.4 |
| 40 | C | 1 | 20.617 |  |
| 40 | B | 2.5 | 0.638 | 96.6 |
| 40 | C | 2.5 | 18.817 |  |
| 40 | B | 4 | 0.647 | 96.8 |
| 40 | C | 4 | 20.323 |  |

Matrix Interference

Although excipient and matrix interference was addressed in the specificity section, a matrix spiking study was performed to ensure that upstream matrix does not bias the results. A plasma derived-Alpha-1 (PD Alpha-1) sample that contains different matrices was added to cell culture media and the percent capping measured using the method described herein. The media selected for the experiment contained the highest level of additives used in upstream development experiments, such as CDM4PERMAB™ media (Hyclone), Pluronic® F-68 (BASF), Antifoam-C (Dow Corning®), and various cell culture media. Plasma derived Alpha-1 was added to the media at a 0.5 mg/mL concentration. The sample was then prepared using the typical clean-up procedure of buffer exchanging into 20 mM phosphate, pH 7 followed by 10 kDa spin filtering. The capping percent of the PD Alpha-1 added to culture media was compared to capping results for PD Alpha-1 that was not added to cell culture media (see Table 22). The results show a percent capping of 99.4% for the PD Alpha-1 added to the media and 99.2% (average) for the PD Alpha-1 not added to media, which was well within the intermediate precision associated with this method. These results indicate that the cell culture media does not interfere with the assay after samples have undergone the appropriate clean-up steps.

TABLE 22

Results for Matrix Interference

| Sample | Reaction | Corrected Area | Percent Capping |
|---|---|---|---|
| PD Alpha-1 (in culture media) | A | 0.006 | 99.4 |
| PD Alpha-1 (in culture media) | B | 0.012 |  |
| PD Alpha-1 (in culture media) | C | 1.064 |  |
| PD Alpha-1, Day 1 | A | 0.000 | 99.0 |
| PD Alpha-1, Day 1 | B | 0.020 |  |
| PD Alpha-1, Day 1 | C | 2.132 |  |
| PD Alpha-1, Day 2 | A | 0.000 | 99.3 |
| PD Alpha-1, Day 2 | B | 0.017 |  |
| PD Alpha-1, Day 2 | C | 2.330 |  |

SUMMARY

The results obtained from the development and pre-qualification experiments are summarized in Table 23. Based on the above studies, this method was optimized for the determination of the capping rate in protein samples. The linearity, LOQ, precision, accuracy, and robustness parameters determined for this assay show that this method was consistent, accurate, and reliable.

TABLE 23

Summary of Method Parameters

| Parameters | Experiment | Results |
|---|---|---|
| Linearity | Six standard curves of peak area vs galactose (8 to 1500 pmol) | $R^2 \geq 0.99$ |
| Range | Working range of protein concentration | $\leq 1.5$ mg/mL |

TABLE 23-continued

Summary of Method Parameters

| Parameters | Experiment | Results |
|---|---|---|
| LOQ | | 8 pmol galactose/injection |
| Repeatability | Six sample replicates on same day/same instrument | 0.20% RSD |
| Intermediate Precision | Calculated capping based on three days, two columns, three electrodes, and two ICS 3000 systems | 0.25% RSD for recAlpha-1 samples; 2.99% for fetuin control |
| Accuracy | Closeness of average fetuin value to pre-established value | 97-103% recovery |
| Robustness | Sample stability at 10° C. for 48 hrs | No effect |
| | Enzyme reaction time 2 to 4 hours | No effect |

What is claimed is:

1. A method for determining the percentage of capped galactose in a glycoprotein, comprising:
   (a) preparing a glycoprotein in a medium for analysis, whereby a protein preparation is obtained;
   (b) preparing enzymatically treated protein samples and a control from the prepared protein comprising:
   Dividing the protein preparation into a plurality of protein samples;
      (i) adding no enzyme to at least one protein sample as a media sample background control, whereby sample A is obtained;
      (ii) adding at least β-galactosidase to at least one protein sample, whereby sample B is obtained;
      (iii) adding at least β-galactosidase and α-sialidase to at least one other protein sample, whereby sample C is obtained; and
   incubating the plurality of protein samples comprising samples A, B, and C;
   (c) quantifying the galactose amount in each of samples A, B, and C using HPAEC-PAD chromatography, wherein the galactose amount in sample A reflects the amount of galactose from the medium, wherein the galactose amount in sample B reflects the amount of galactose uncapped with a sialic acid residue in the protein preparation in addition to the amount of galactose from the medium, and wherein the galactose amount in sample C reflects the amount of galactose capped with a sialic acid in addition to the amount of galactose from the medium and uncapped by sialic acid; and
   (d) determining the percentage of capped galactose in the glycoprotein based on the galactose amounts in sample A, sample B, and sample C, wherein the method has a linearity of $R^2 \geq 0.99$.

2. The method of claim 1, further comprising:
   (f) analyzing a plurality of positive and negative controls using HPAEC-PAD chromatography;
   (g) analyzing a plurality of standards using HPAEC-PAD chromatography; and
   (h) comparing the plurality of protein samples to the plurality of standards and controls.

3. The method of claim 1, wherein the method has an accuracy of 97-103% recovery.

4. The method of claim 1, wherein the method has a repeatability of 0.20% RSD.

5. The method of claim 1, wherein each of the plurality of protein samples has a protein concentration of ≤1.5 mg/mL.

6. The method of claim 1, wherein the glycoprotein is recombinant alpha-1 proteinase inhibitor (recAlpha-1).

7. The method of claim 6, wherein the recAlpha-1 is secreted by PerC6 cells and has N-linked glycan carbohydrate structures capped by terminal sialic acids (N-acetylneuraminic acids).

* * * * *